US006864379B2

(12) United States Patent
Petersen et al.

(10) Patent No.: US 6,864,379 B2
(45) Date of Patent: Mar. 8, 2005

(54) STEPWISE ALKYLATION OF 5-SUBSTITUTED 1-(4-FLUOROPHENYL)-1,3-DIHYDROISOBENZOFURANS

(75) Inventors: Hans Petersen, Vanløse (DK); Haleh Ahmadian, Solrød Strand (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/242,804

(22) Filed: Sep. 10, 2002

(65) Prior Publication Data

US 2003/0083509 A1 May 1, 2003

Related U.S. Application Data

(63) Continuation of application No. PCT/DK01/00159, filed on Mar. 9, 2001.

(30) Foreign Application Priority Data

Mar. 13, 2000 (DK) ......................................... 2000 00403
Mar. 14, 2000 (DK) ......................................... 2000 00414

(51) Int. Cl.$^7$ .................... C07D 307/78; C07D 307/87; C07D 307/93
(52) U.S. Cl. ...................... 549/467; 549/466; 549/468; 549/469; 549/471
(58) Field of Search ................................ 549/467, 466, 549/468, 469, 471

(56) References Cited

U.S. PATENT DOCUMENTS

| 3,467,675 | A | 9/1969 | Petersen et al. ......... 260/346.2 |
|---|---|---|---|
| 4,136,193 | A | 1/1979 | Bogeso et al. ............... 424/285 |
| 4,650,884 | A | 3/1987 | Bogeso ....................... 549/467 |
| 4,943,590 | A | 7/1990 | Boegesoe et al. ........... 514/469 |
| 5,296,507 | A | 3/1994 | Tanaka et al. .............. 514/465 |
| 6,020,501 | A | 2/2000 | Massonne et al. .......... 549/307 |
| 6,028,204 | A | 2/2000 | Massonne et al. .......... 549/307 |
| 6,229,026 | B1 | 5/2001 | Petersen ..................... 549/467 |
| 6,258,842 | B1 | 7/2001 | Petersen et al. ............ 514/469 |
| 6,291,689 | B1 | 9/2001 | Petersen et al. ............ 549/467 |
| 6,310,222 | B1 | 10/2001 | Ikemoto et al. ............. 549/467 |
| 6,365,747 | B1 | 4/2002 | Dall'Asta et al. ........... 548/146 |
| 6,392,060 | B2 | 5/2002 | Petersen et al. ............ 549/307 |
| 6,403,813 | B1 | 6/2002 | Petersen et al. ............ 549/305 |
| 6,407,267 | B1 | 6/2002 | Rock et al. ................. 549/467 |
| 6,420,574 | B2 | 7/2002 | Petersen et al. ............ 549/467 |
| 6,426,422 | B1 | 7/2002 | Petersen et al. ............ 549/467 |
| 6,433,196 | B1 | 8/2002 | Ikemoto et al. ............. 549/469 |
| 6,441,201 | B1 | 8/2002 | Weber ........................ 549/468 |
| 6,458,973 | B1 | 10/2002 | Dall'Asta et al. ........... 549/305 |
| 2002/0004604 | A1 | 1/2002 | Petersen et al. ............ 549/462 |
| 2002/0026062 | A1 | 2/2002 | Petersen et al. ............ 549/467 |
| 2002/0035277 | A1 | 3/2002 | Rock et al. ................. 549/467 |
| 2002/0040153 | A1 | 4/2002 | Petersen ..................... 549/467 |
| 2002/0061925 | A1 | 5/2002 | Petersen et al. ............ 514/469 |
| 2002/0077353 | A1 | 6/2002 | Petersen et al. ............ 514/469 |
| 2002/0087012 | A1 | 7/2002 | Castellin et al. ............ 549/467 |
| 2002/0120005 | A1 | 8/2002 | Villa et al. .................. 514/466 |
| 2002/0128497 | A1 | 9/2002 | Bolzonella et al. ......... 549/467 |

FOREIGN PATENT DOCUMENTS

| WO | 98/19511 | 5/1998 | |
|---|---|---|---|
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |
| WO | 01/45483 | 6/2001 | |
| WO | 01/47877 | 7/2001 | |
| WO | 01/47909 | 7/2001 | ......... C07D/307/87 |
| WO | 01/49672 | 7/2001 | ......... C07D/307/87 |
| WO | 01/51477 | 7/2001 | ......... C07D/307/87 |
| WO | 01/51478 | 7/2001 | ......... C07D/307/87 |
| WO | 01/62754 | 8/2001 | ......... C07D/307/87 |
| WO | 01/66536 | 9/2001 | ......... C07D/307/87 |
| WO | 01/68628 | 9/2001 | ......... C07D/307/87 |
| WO | 01/68630 | 9/2001 | ......... C07D/307/87 |
| WO | 01/68631 | 9/2001 | ......... C07D/307/87 |
| WO | 01/68632 | 9/2001 | ......... C07D/307/87 |
| WO | 01/85712 | 11/2001 | ......... C07D/307/87 |
| WO | 02/04435 | 1/2002 | ......... C07D/307/87 |

OTHER PUBLICATIONS

U.S. patent application Ser. No. 10/183,958, filed Jun. 25, 2002.
U.S. patent application Ser. No. 10/186,337, filed Jun. 27, 2002.
U.S. patent application Ser. No. 10/191,808, filed Jul. 8, 2002.
U.S. patent application Ser. No. 10/232,994, filed Aug. 29, 2002.
U.S. patent application Ser. No. 10/237,145, filed Sep. 5, 2002.
U.S. patent application Ser. No. 10/238,907, filed Sep. 6, 2002.
U.S. patent application Ser. No. 10/228,388, filed Aug. 23, 2002.
U.S. patent application Ser. No. 10/238,843, filed Sep. 9, 2002.
U.S. patent application Ser. No. 10/233,132, filed Aug. 30, 2002.
U.S. patent application Ser. No. 10/291,174, filed Nov. 8, 2002.
Levy, L.F., "4–Aminophthalide and Some Derivatives", *J. Chem. Soc.* pp. 867–870 (1931).
Tirouflet, Jean, "Phtalide Substitués en 5", *Bull. Soc. Sci. de Bretagne* 26:35–43 (1951).

(List continued on next page.)

*Primary Examiner*—Ba K. Trinh
(74) *Attorney, Agent, or Firm*—Darby & Darby

(57) ABSTRACT

Methods for manufacture of citalopram through stepwise alkylation of 5-substituted 1-(4-fluorophenyl)-1,3-dihydroisobenzofurans are disclosed.

20 Claims, No Drawings

OTHER PUBLICATIONS

Forney, LeRoy S.., "Reaction of Terephthalic Acid with Formaldehyde in Sulfur Trioxide Media," *J. Org. Chem.* 35:1695–1696 (1970).

Dordor, Isabelle M. et al., "Reaction of Oxazolines with Phosphorus Oxychloride," *Tetrahedron Letters* 24:1437–1440 (1983).

Barton, Sir Derek et al., *Comprehensive Organic Chemistry. The Synthesis and Reactions of Organic Compounds*, vol. 2, pp. 1024–1025.

U.S. patent application Ser. No. 10/191,808, filed Jul. 8, 2002.

U.S. patent application Ser. No. 10/232,994, filed Aug. 29, 2002.

U.S. patent application Ser. No. 10/237,145, filed Sep. 5, 2002.

U.S. patent application Ser. No. 10/238,907, filed Sep. 6, 2002.

U.S. patent application Ser. No. 10/228,388, filed Aug. 23, 2002.

U.S. patent application Ser. No. 10/238,843, filed Sep. 9, 2002.

U.S. patent application Ser. No. 10/233,132, filed Aug. 30, 2002.

U.S. patent application Ser. No. 10/291,174, filed Nov. 8, 2002.

Levy, L.F., "4–Aminophthalide and Some Derivatives", *J. Chem. Soc.* pp. 867–870 (1931).

Tirouflet, Jean, "Phtalide Substitués en 5", *Bull. Soc. Sci. de Bretagne* 26:35–43 (1951).

Forney, LeRoy S.., "Reaction of Terephthalic Acid with Formaldehyde in Sulfur Trioxide Media," *J. Org. Chem.* 35:1695–1696 (1970).

Dordor, Isabelle M. et al., "Reaction of Oxazolines with Phosphorus Oxychloride," *Tetrahedron Letters* 24:1437–1440 (1983).

Barton, Sir Derek et al., *Comprehensive Organic Chemistry. The Synthesis and Reactions of Organic Compounds*, vol. 2, pp. 1024–1025, 1978.

Bigler, Allan et al., Quantitative Structure–activity Relationships in a Series of Selective 5–HT uptake inhibitors, *Eur. J. Med. Chem.* 3:289–295 (1997).

STEPWISE ALKYLATION OF 5-SUBSTITUTED 1-(4-FLUOROPHENYL)-1,3-DIHYDROISOBENZOFURANS

This application is a continuation of International application no. PCT/DK01/00159, filed Mar. 9, 2001. The prior application is hereby incorporated by reference in its entirety.

The present invention relates to a method for the preparation of the well-known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some years and has the following structure:

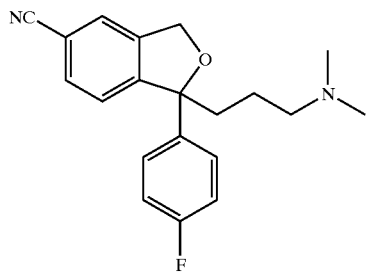

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A-474580.

Citalopram was first disclosed in DE No. 2,657,013, corresponding to U.S. Pat. No. 4,136,193. This patent publication describes the preparation of citalopram by one method and outlines a further method, which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

International patent application No. WO 98/019511 discloses a process for the manufacture of citalopram wherein a 4-(cyano, alkyloxycarbonyl or alkylaminocarbonyl)-2-hydroxy-methylphenyl-(4-fluorophenyl)methanol compound is subjected to ring closure. The resulting 5-(alkyloxycarbonyl or alkylaminocarbonyl)-1-(4-fluorophenyl)-1,3-dihydroisobenzofuran is converted to the corresponding 5-cyano derivative and the 5-cyano derivative is then alkylated with a (3-dimethylamino)propyl halogenide in order to obtain citalopram.

It has now, surprisingly, been found that citalopram may be manufactured by a novel favourable process where a 5-substituted 1-(4-fluorophenyl)-1,3-dihydroisobenzofuran is derivatised by stepwise addition of the 3-dimethylaminopropyl chain. Optionally, and dependent upon the nature of the substituent in the 5-position, said substituent is converted into a cyano-group at a suitable time in the reaction sequence.

SUMMARY OF THE INVENTION

The invention comprises the following:

A method for preparation of citalopram, comprising subjecting the compound of formula I

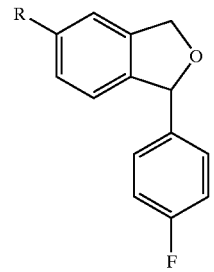

wherein R represents CN, OH, O-triflate, halogen, $NHR^5$ wherein $R^5$ is selected from hydrogen and $C_{1-6}$ alkylcarbonyl, CHO, $CO_2R^6$, $CONHR^7$ wherein $R^6$–$R^7$ are each independently selected from hydrogen and $C_{1-6}$ alkyl, or R is a oxazoline or a thiazoline of the formula

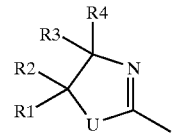

wherein U is O or S;
$R^1$–$R^2$ are each independently selected from hydrogen and $C_{1-6}$ alkyl, or $R^1$ and $R^2$ together form a $C_{2-5}$ alkylene chain thereby forming a spiro ring; $R^3$ is selected from hydrogen and $C_{1-6}$ alkyl, $R^4$ is selected from hydrogen, $C_{1-6}$ alkyl, a carboxy group or a precursor group therefore, or $R^3$ and $R^4$ together form a $C_{2-5}$ alkylene chain thereby forming a spiro ring;
to a stepwise addition of reagents which eventually lead to the 3-(N,N-dimethylamino)-prop-1-yl substituent in citalopram. Optionally, if R is not CN, it is converted into a CN group at a suitable time in the reaction sequence.

The first aspect of the invention comprises addition of a C-1 chain:

This reaction comprises the following subsequent steps, some of which may be performed together and the order of which may be changed in ways known to those skilled in the art:

a) addition of a C-1 chain;
b) addition of a C-2-chain, which is optionally activated with regard to step c) or includes simultaneous addition of $NMe_2$ or precursor thereof;
c) addition of $NMe_2$ or precursor thereof;
d) (optional) adjusting of oxidation level;
e) (optional) conversion of R to a 5-cyano-group; and
f) (optional) conversion of $NMe_2$-precursor to $NMe_2$.

In one preferred embodiment of the above, the following steps are undertaken:

a) addition of the C-1 chain;
b) addition of C-2 chain and of dimethylamino-substituent;
c) adjustment of oxidation level (one-pot process with b)); and
e) (optional) derivatising the substitutent R to a 5-cyano-group.

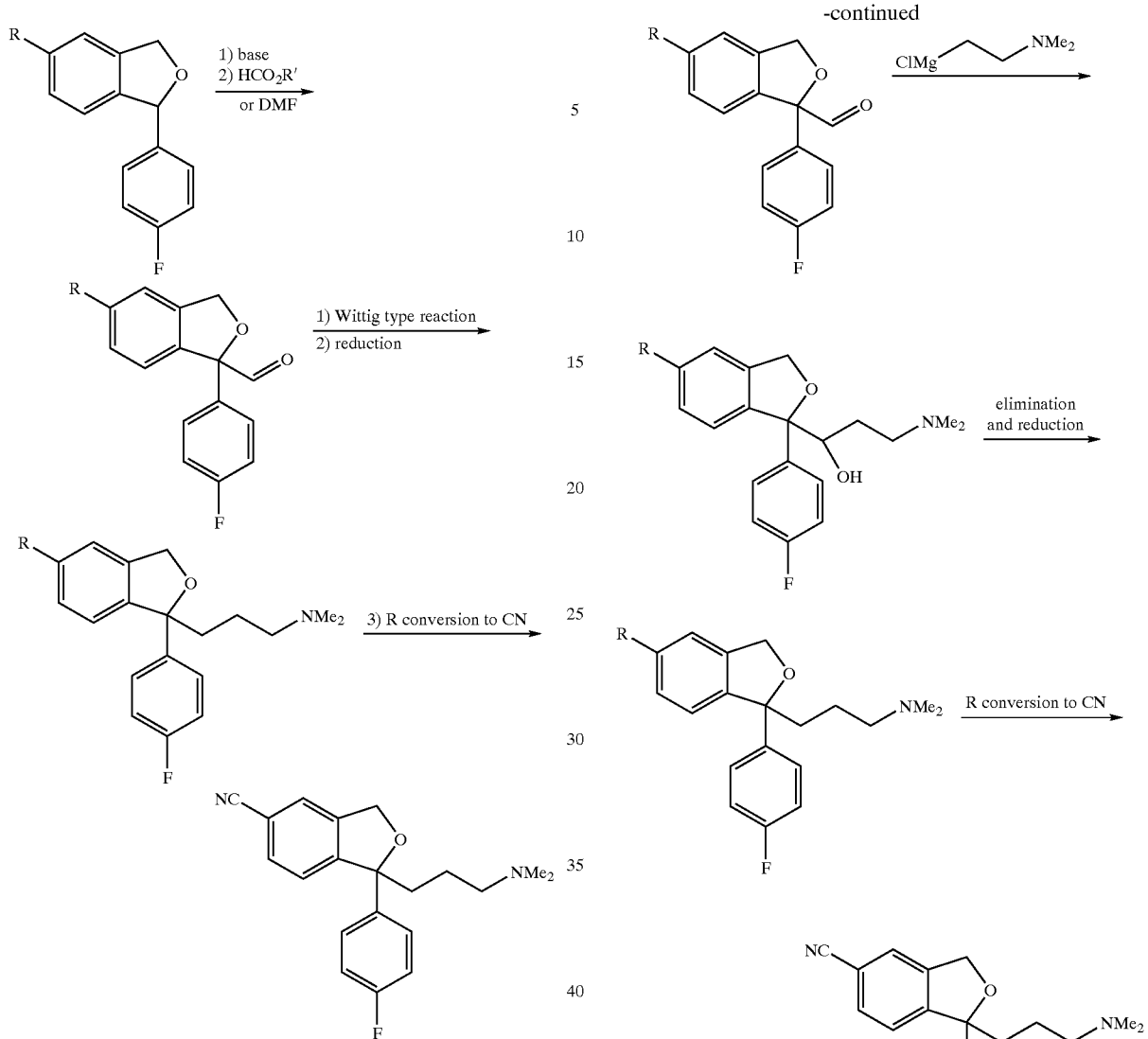

The Wittig reaction is known in the art and comprises an ylide derivative of suitable structure in the present invention an ylide such as Ph₃P=CH—CH₂NMe₂. The product of this reaction contains a double bond which is reduced by methods known in the art.

In another embodiment of the invention the following steps are performed:
a) addition of the C-1;
b) Grignard reaction;
c) elimination and reduction; and
d) (optional) conversion of R to 5-cyano-group.

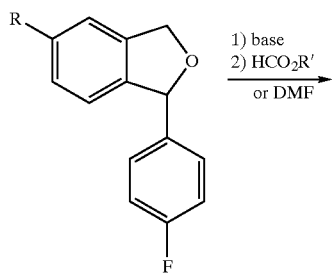

which are followed by a Grignard reaction. The product from the Grignard reaction is a secondary alcohol, which is subjected to elimination and subsequent reduction of the resulting double bond. Reduction of the double bond is performed by standard methods. Another aspect of the invention involves reacting the compound of formula I as above by addition of a C-2 chain. This aspect of the invention comprises the following steps some of which are performed together:

a) addition of C-2-chain;
b) addition of C-1 which is optionally activated with regard to step c);
c) addition of NMe₂ or a precursor for this group;
d) optionally adjusting oxidation level; and
e) (optional) derivatising R to 5-cyano substituent.

In one preferred embodiment of the invention, the following steps are performed:
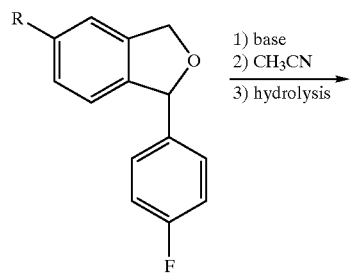
1) base
2) CH$_3$CN
3) hydrolysis
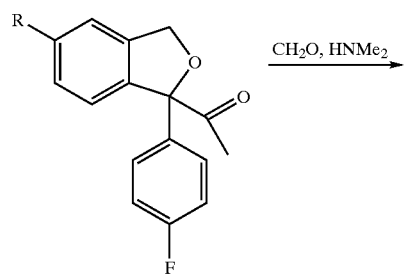
CH$_2$O, HNMe$_2$
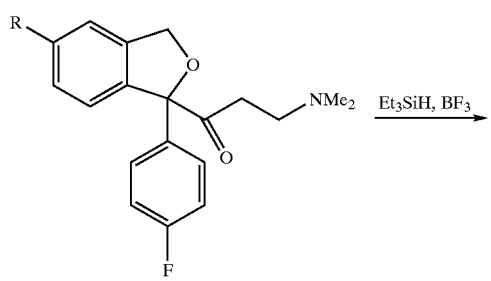
Et$_3$SiH, BF$_3$
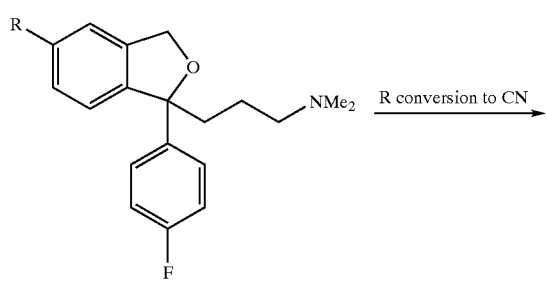
R conversion to CN
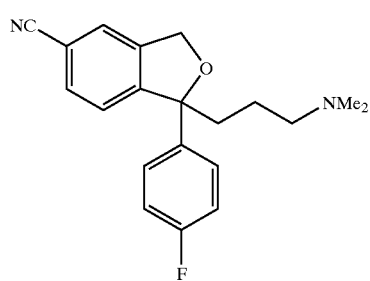
In another preferred embodiment of the invention, the following steps are performed
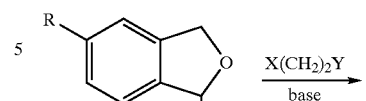
X(CH$_2$)$_2$Y
base
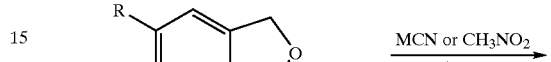
MCN or CH$_3$NO$_2$
base
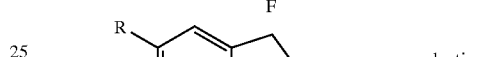
reduction
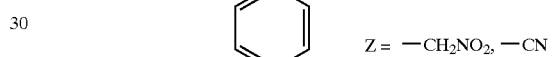
Z = —CH$_2$NO$_2$, —CN
dimethylation
R to CN conversion
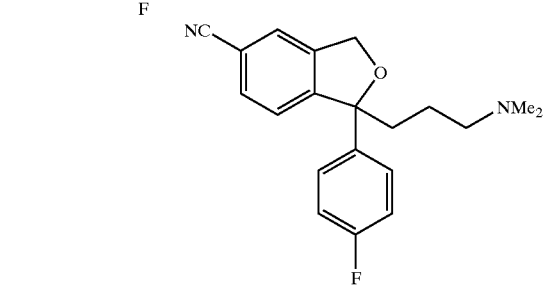

In yet another embodiment of the invention, the following reactions are performed:

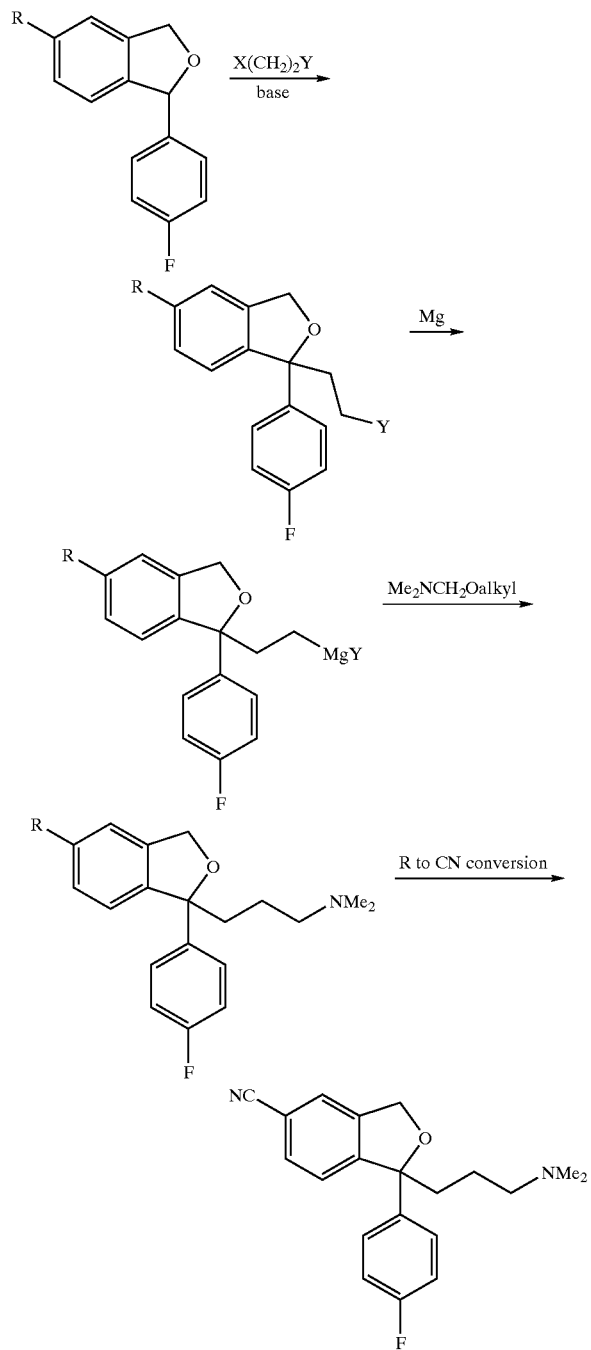

Reduction of the nitro group can be performed by methods known in the art. One preferred method is $H_2$ in the presence of Pd/C.

MCN represents metal cyanide such as NaCN, KCN, $Zn(CN)_2$ or CuCN.

Methylation of the amino group can be performed by inter alia $CH_3I$ or by reductive amination of formaldehyde. Preferred reductive compounds are $NaBH_4$ or $NaCNBH_3$.

DETAILED DESCRIPTION OF THE INVENTION

The starting material of formula (I) may be prepared as described in U.S. Pat. No. 4,136,193 or as described in WO 98/019511.

The first addition step where the compound of formula I is reacted with a C-1 or C-2 reagent, is suitably carried out by treatment of the compound of formula (I) with a base such as for example LDA (lithiumdiisopropylamine), LiHMDS, NaH, NaHMDS, and NaOMe in an aprotic organic solvent such as THF (tetrahydrofuran), DMF (dimethylformamide), NMP (N-methylpyrrolidon), ethers such as diethylether, or dioxalane, toluene, benzene, or alkanes and mixtures thereof followed by addition of the C-1 or C-2 reagent.

As used herein, a 'C-1 (C-2) reagent' is a reagent which in a chemical reaction is capable of adding a C-1 (C-2) fragment to a molecule.

Reductions can be performed by the methods known in the art.

The methods for converting the group R into a cyano substituent can be any of the following methods:

(i) R is O-triflates or halogen

When R is halogen or O-triflates of the formula $CF_3$—$(CF_2)_n$—$SO_2$— wherein n is an integer in the range 0–8, incl., the conversion to a cyano group may be carried out by reaction with a cyanide source, for example KCN, NaCN, CuCN, $Zn(CN)_2$ or $(R^8)_4NCN$ where $(R^8)_4$ indicates four groups which may be the same or different and are selected from hydrogen and straight chain or branched $C_{1-6}$ alkyl, in the presence of a palladium catalyst and a catalytic amount of $Cu^+$ or $Zn^{2+}$, or with $Zn(CN)_2$ in the presence of a palladium catalyst.

The cyanide source is used in a stoichiometric amount or in excess, preferably 1–2 equivalents are used pr. equivalent starting material. $(R^8)_4N^+$ may conveniently be $(Bu)_4N^+$. The cyanide compound is preferably NaCN or KCN or $Zn(CN)_2$.

The palladium catalyst may be any suitable Pd(0) or Pd(II) containing catalyst, such as $Pd(PPh_3)_4$, $Pd_2(dba)_3$, $Pd(PPh_3)_2Cl_2$, etc. The Pd catalyst is conveniently used in an amount of 1–10, preferably 2–6, most preferably about 4–5 mol %.

Catalytic amounts of $Cu^+$ and $Zn^{2+}$, respectively, means substoichiometric amounts such as 0.1–5, preferably 1–3 eq. % relative to reactants. Conveniently, about ½ eq. is used per eq. Pd. Any convenient source of $Cu^+$ and $Zn^{++}$ may be used. $Cu^+$ is preferably used in the form of CuI and $Zn^{2+}$ is conveniently used as the $Zn(CN)_2$ salt.

When R is Br or I, the conversion to a cyano group also may be carried out by reaction with Cu(CN) without catalyst. In a preferred embodiment, the reaction is performed at elevated temperature.

In another aspect of the invention, the reaction is performed in an ionic liquid of the general formula $(R^9)_4N^+$, $X^-$, wherein $R^9$ are alkyl-groups or two of the $R^9$ groups together form a ring and $X^-$ is the counterion. In one embodiment of the invention, $(R^9)_4N^+X^-$ represents the ring

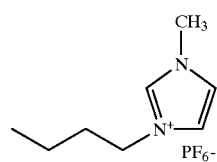

In another particular aspect, the reaction is conducted with apolar solvents such as benzene, xylene or mesitylene and under the influence of microwaves by using i.e. Synthewave 1000™ by Prolabo. In a particular aspect, the reaction is performed without added solvent.

The temperature ranges are dependent upon the reaction type. If no catalyst is present, preferred temperatures are in the range of 100–200° C. However, when the reaction is conducted under the influence of microwaves, the temperature in the reaction mixture may raise to above 300° C. More preferred temperature ranges are between 120–170° C. The most preferred range is 130–150° C.

If a catalyst is present, the preferred temperature range is between 0 and 100° C. More preferred are temperature ranges of 40–90° C. Most preferred temperature ranges are between 60–90° C.

Other reaction conditions, solvents, etc. are conventional conditions for such reactions and may easily be determined by a person skilled in the art.

When R is Cl or Br, the conversion to a cyano group may also be carried out by reaction with a cyanide source, for example KCN, NaCN, CuCN, $Zn(CN)_2$ or $((R^8)_4N)CN$ where $(R^8)_4$ indicates four groups which may be the same or different and are selected from hydrogen and straight chain or branched $C_{1-6}$ alkyl, in the presence of a nickel catalyst.

The nickel catalyst may be any suitable Ni(0) or Ni(II) containing complex which acts as a catalyst, such as $Ni(PPh_3)_3$, $(\eta\text{-aryl})\text{-Ni}(PPh_3)_2Cl$, etc. The nickel catalysts and their preparation are described in WO 96/11906, EP-A-613720 or EP-A-384392.

In one embodiment of the invention, the reaction is carried out in the presence of a catalytic amount of $Cu^+$ or $Zn^{2+}$.

In a particularly preferred embodiment, a nickel(0) complex is prepared in situ before the cyanation reaction by reduction of a nickel(II) precursor such as $NiCl_2$ or $NiBr_2$ by a metal, such as zinc, magnesium or manganese in the presence of excess of complex ligands, preferably triphenylphosphin.

The Ni-catalyst is conveniently used in an amount of 0.5–10, preferably 2–6, most preferably about 4–5 mol %.

Catalytic amounts of $Cu^+$ and $Zn^{2+}$, respectively, means substoichiometric amounts such as 0.1-5, preferably 1–3 eq. %. Any convenient source of $Cu^+$ and $Zn^{2+}$ may be used. $Cu^+$ is preferably used in the form of CuI and $Zn^{2+}$ is conveniently used as the $Zn(CN)_2$ salt or formed in situ by reduction of a Nickel (II) compounds using zinc.

The Ni catalysts are i.e. Ni (0), Pd(0) or Pd(II) catalysts as described by Sakakibara et. al. in *Bull Chem. Soc. Jpn.* 1988, 61, 1985–1990. Preferred catalysts are $Ni(PPh_3)_3$ or $Pd(PPh_3)_4$, or $Pd(PPh)_2Cl_2$.

The reactions may be performed in any convenient solvent as described in Sakakibara et. al. in *Bull. Chem. Soc. Jpn.* 1988, 61, 1985–1990. Preferred solvents are acetonitrile, ethylacetate, THF, DMF or NMP.

R is an oxazoline or thiazoline.

When R is an oxazoline or a thiazoline of the formula

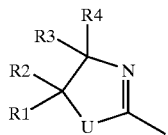

wherein U is O or S;

$R^1$-$R^4$ are each independently selected from hydrogen and $C_{1-6}$ alkyl, or $R^3$ and $R^4$ together form a $C_{2-5}$ alkylene chain thereby forming a spiro ring; $R^1$ is selected from hydrogen and $C_{1-6}$ alkyl, $R^2$ is selected from hydrogen, $C_{1-6}$ alkyl, a carboxy group or a precursor group therefore, or $R^1$ and $R^2$ together form a $C_{2-5}$ alkylene chain thereby forming a Spiro ring; the conversion to a cyano group may be carried out by dehydration or alternatively where U is S, thermal cleavage of the thiazoline ring or treatment with a radical initiator, such as peroxide or with light.

The dehydration agent may be any suitable dehydration agent conventionally used in the art, such as phosphoroxytrichloride, thionylchloride, phosphorpentachloride, PPA (polyphosphoric acid) and $P_4O_{10}$. The reaction may be carried out in the presence of an organic base, such as pyridine.

Alternatively, the dehydration agent may be a Vilsmeier reagent, i.e. a compound which is formed by reaction of a chlorinating agent, preferably an acid chloride, e.g. phosgene, oxalyl chloride, thionyl chloride, phosphoroxychloride, phosphorpentachloride, trichloromethyl chloroformate, also briefly referred to as "diphosgene", or bis(trichloromethyl) carbonate, also briefly referred to as "triphosgene", with a tertiary amide such as N,N-dimethylformamide or a N,N-dialkylalkanamide, e.g N,N-dimethylacetamide. A classic Vilsmeyer reagent is the chloromethylenedimethyliminium chloride. The Vilsmeier reagent is preferably prepared in situ by adding the chlorinating agent to a mixture containing the starting oxazoline or thiazoline derivative and the tertiary amide.

When U is S and the conversion of the thiazoline group into the cyano group is made by thermal transformation, the thermal decomposition of the thiazoline is preferably carried out in an anhydrous organic solvent, more preferably an aprotic polar solvent, such as N,N-dimethylformamide, N,N-dimethylacetamide, dimethylsulfoxide or acetonitrile. The temperature at which the thermal decomposition transforms the 2-thiazolyl group to a cyano group is between 60° C. and 140° C. The thermal decomposition may conveniently be carried out by reflux in a suitable solvent, preferably acetonitrile. The thermal cleavage may conveniently be carried out in the presence of oxygen or an oxidation agent. A thiazoline group where U is S and $R^3$ or $R^4$ is a carboxy group or a precursor for a carboxy group can also be converted to citalopram by treatment with a radical initiator such as light or peroxides.

R is CHO, $CO_2R^6$ or $CONHR^7$

When R is CHO, the conversion to a cyano group may be carried out by conversion of the formyl group to an oxime or similar group by reaction with a reagent $R^{10}$—V—$NH_2$ wherein $R^{10}$ is hydrogen, lower alkyl, aryl or heteroaryl and V is O, N or S, followed by conversion to a cyano group by a common dehydrating agent, for example thionylchloride, acetic anhydride/pyridine, pyridine/HCl or phosphor pentachloride. Preferred reagents $R^{10}$—V—$NH_2$ are hydroxylamine and compounds wherein $R^{10}$ is alkyl or aryl and V is N or O.

When R is —$COOR^6$, the conversion to a cyano group may be carried out via the corresponding acid chloride, or ester and amide.

The acid chloride is conveniently obtained by treatment of the acid with $POCl_3$, $PCl_5$ or $SOCl_2$ neat or in a suitable solvent, such as toluene or toluene comprising a catalytic amount of N,N-dimethylformamide. The ester is obtained by treatment of the acid with an alcohol $R^6$—OH, wherein $R^6$ is as defined above, in the presence of an acid, preferably a mineral acid or a Lewis acid, such as HCl, $H_2SO_4$, $POCl_3$, $PCl_5$ or $SOCl_2$. Alternatively, the ester may be obtained from the acid chloride by reaction with an alcohol. The ester or the acid chloride is then converted to an amide by amidation with ammonia or an $C_{1-6}$ alkylamine, preferably t-butyl amine.

The conversion to amide may also be obtained by reaction of the ester with ammonia or an alkylamine under pressure and heating.

The amide group is then converted to a cyano group by dehydration. The dehydrating agent may be any suitable dehydrating agent, and the optimal agent may easily be determined by a person skilled in the art. Examples of suitable dehydrating agents are $SOCl_2$, $POCl_3$ and $PCl_5$, preferably $SOCl_2$.

In a particularly preferred embodiment, the carboxylic acid is reacted with an alcohol, $R^6OH$, preferably ethanol, in the presence of $POCl_3$, in order to obtain the corresponding ester, which is then reacted with ammonia thereby giving the corresponding amide, which in turn is reacted with $SOCl_2$ in toluene comprising a catalytic amount of N,N-dimethylformamide.

Alternatively, a compound where R is —COOH may be reacted with chlorosulfonyl isocyanate in order to form the nitrile, or treated with a dehydrating agent and a sulfonamide as described in PCT/DK/0000032.

R is $NHR^5$.

When R is —$NHR^5$, where $R^5$ is hydrogen, the conversion into cyano is preferably performed by diazotation and followed by reaction with $CN^-$. Most preferably $NaNO_2$ and CuCN and/or NaCN are used. When $R^5$ is $C_{1-6}$ alkylcarbonyl, it is initially subjected to hydrolysis thereby obtaining the corresponding compound wherein $R^5$ is H which is then converted as described above. The hydrolysis may be performed either in acidic or basic environment.

Citalopram may be used as the free base or as a pharmaceutically acceptable acid addition salt thereof. As acid addition salts, such salts formed with organic or inorganic acids may be used. Examples of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Throughout the specification and claims, the term alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Similarly, alkenyl and alkynyl, respectively, designate such groups having from two to six carbon atoms, including one double bond and triple bond respectively, such as ethenyl, propenyl, butenyl, ethynyl, propynyl, and butynyl.

The term aryl refers to a mono- or bicyclic carbocyclic aromatic group, such as phenyl and naphthyl, in particular phenyl.

The term aralkyl refers to aryl-alkyl, wherein aryl and alkyl is as defined above.

Halogen means chloro, bromo or iodo.

EXAMPLE

Synthesis of Citalopram via 1-(4-fluorophenyl)-1-formyl-1, 3-dihydro-5-isobenzofurancarbonitrile:

1-(4-Fluorophenyl)-1-formyl-1,3-dihydro-5-isobenzofurancarbonitrile. A solution of 1-(4-fluorophenyl)-1,3-dihydro-5-isobenzofurancarbonitrile (2.4 g, 10 mmol) in THF (15 mL) was added to a solution of LDA (11 mmol) in THF (25 mL) at −78° C. under an atmosphere of nitrogen. The mixture was allowed to warm to −40° C. during 45 min. Freshly distilled methyl formate (0.75 mL, 12 mmol) was added at this temperature, and stirring was continued for 1 h while warming to 0° C. Then the mixture was poured into ice/saturated ammonium chloride solution, and extracted with $Et_2O$ (3×100 mL). The organic extracts were washed with brine, dried and evaporated. Silica gel chromatography (heptane, EtOAc 4:1) of the residue gave the product (1.3 g, 50%). 1H NMR (CDCl3) δ 5.35 (2H, s); 7.10 (2H, t, J=9.0 Hz); 7.50 (1H, dd, J=5.2 and 9.0 Hz); 7.57 (1H, s); 7.60 (1H, d, J=8.0 Hz); 7.70 (1H, d, J=8.0 Hz).

1-[2-(Ethoxycarbonyl)ethyl]-1-(4-fluorophenyl)-1,3-dihydro-5-isobenzofurancarbonitrile. Triethyl phosphonoacetate (5.1 mL, 22.8 mmol) was added to a solution of LDA (22.8 mmol) in THE (100 mL) at −30° C. under an atmosphere of nitrogen. The mixture was stirred at this temperature for 1 h, then a solution of 1-(4-fluorophenyl)-1-formyl-1,3-dihydro-5-isobenzofurancarbonitrile (5.8 g, 21.7 mmol) in THE (50 mL) was added. The mixture was allowed to warm to room temperature during 2.5 h, then poured into ice/H20. The pH was adjusted to about 5 by addition of acetic acid and the aqueous phase was extracted with iEt2O, dried and evaporated. The crude product (8.0 g) was hydrogenated in ethanol (150 mL) using Pt/C (1.7 g, 5%) as catalyst. After 16 h, the mixture was filtered through Celite and evaporated. Silica gel chromatography (heptane, EtOAc 5:1) afforded the product as an oil (4.2g. 57%). 1H NMR (CDCl3) δ 1.20 (3H, t, J=7.0 Hz); 2.25 (2H, m); 2.50 (2H, m); 4.05 (2H, q, J=7.0 Hz); 5.15 (1H, d, J=12.7 Hz); 5.19 (1H, d, J=12.7 Hz); 7.02 (2H, t, J=9.0 Hz); 7.40 (3H, m); 7.50 (1H, s); 7.60 (1 H, d, J=8.0 Hz).

[2-(N,N-Dimethylamido)ethyl]-1-(4-fluorphenyl)-1,3-dihydro-5isobenzofuran-carbonitrile. Methyl chloroaluminum dimethylamide (30 mL, 20 mmol, prepared from dimethylammonium chloride and trimethyl aluminum in toluene) was added to a solution of 1-[3-(ethoxycarbonyl) ethyl]-1-(4-fluorophenyl)-1,3-dihydro-5-isobenzofurancarbonitrile (2.6 g, 7.7 mmol) in toluene (50 mL). The resulting mixture was stirred at 50° C. for 19 h, cooled, poured into ice/H$_2$O and extracted with Et$_2$O (3×200 mL). The organic extracts were dried and evaporated to give the product as an oil (2.6 g, 100%). 1H NMR (CDCl3) δ 2.26 (2H, t, J=8.0 Hz); 2.45 (1H, ddd, J=1.8 and 9.9 and 16.0 Hz); 2.59 (1H, ddd, J=8.0 and 14.6 and 16.0 Hz); 2.86(1H, s); 2.88 (1H, s); 5.15 (1H, d, J=13.0Hz);); 5.20 (1H, d, J=13.0 Hz); 7.02 (2H, t, J=8.9 Hz); 7.41 (1H, d, J=8.0 Hz); 7.44 (2H, dd, J=5.2 and 8.9 Hz); 7.50 (1H, s); 7.58 (1H, d, J=8.0 Hz).

What is claimed is:

1. A method for the preparation of citalopram comprising reacting a compound of formula (I)

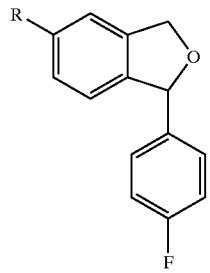

wherein R represents CN, OH, O-triflate, halogen, NHR$^5$ wherein R$^5$ is hydrogen or C$_{1-6}$ alkylcarbonyl, CHO, CO$_2$R$^6$, CONHR$^7$ wherein R$^6$ and R$^7$ each independently are hydrogen or C$_{1-6}$ alkyl or R is a oxazoline or a thiazoline of the formula

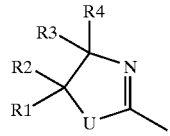

wherein U is O or S;
R$^1$–R$^2$ are each independently selected from hydrogen and C$_{16}$ alkyl, or R$^1$ and R$^2$ together form a C$_{2-5}$ alkylene chain thereby forming a spiro ring; R$^3$ is selected from hydrogen and C$_{1-6}$ alkyl;
R$^4$ is selected from hydrogen, C$_{1-6}$ alkyl, a carboxy group or a precursor group therefor, or
R$^3$ and R$^4$ together form a C$_{2-5}$ alkylene chain thereby forming a spiro ring;
with reagents thereby obtaining a stepwise addition of the 3-(N,N-dimethylamino)propyl substituent.

2. The method of claim 1 wherein a one-carbon group is added initially.

3. The method of claim 1 wherein a two-carbon chain is added initially.

4. The method of claim 1 or 2 wherein the carbon is added by reacting a compound of formula (I) with DMF or HCO$_2$R' in the presence of a base.

5. The method of claim 1 or 2 wherein the carbon is added by reacting a compound of formula (I) with CH$_2$O in the presence of a base.

6. The method of claim 1 or 2 wherein the carbon is added by reacting a compound of formula (I) with CO$_2$ in the presence of a base.

7. The method of claim 6 wherein the carboxyl-derivative is reduced to the hydroxymethyl derivative.

8. The method of claim 1 or 2, wherein the subsequent reactions comprise activation followed by alkylation via cuprate derivatives.

9. The method of claim 6, wherein the subsequent reactions comprise activation followed by alkylation via cuprate derivatives.

10. The method of claim 7, wherein the subsequent reactions comprise activation followed by alkylation via cuprate derivatives.

11. The method of claim 1 or 3 wherein the two carbon chain is added by reaction of the compound of formula (I) with CH$_3$CN in the presence of a base.

12. The method of claim 1 or 3 wherein the two carbon chain is added by reaction of the compound of formula (I) with acetylene.

13. The method of claim 11, wherein the subsequent reactions comprise addition of CH$_2$O and HNMe$_2$.

14. The method of claim 13, wherein the subsequent reactions comprise addition of CH$_2$O and HNMe2.

15. The method of claim 3 wherein the reaction is performed by subjecting a compound of formula I to a base and X(CH$_2$)$_2$Y wherein X and Y are leaving groups.

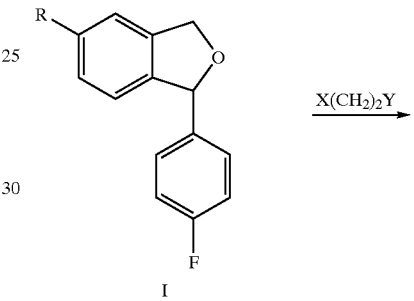

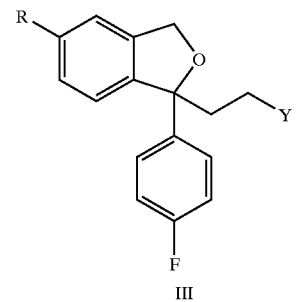

16. The method of claim 15 wherein Y is halogen.

17. The method of claim 1, 3, 15 or 16 wherein the compound III is reacted with MCN or CH$_3$NO$_2$ in the presence of base to form a compound of formula IV which is subsequently reduced and then dimethylated by CH$_3$I or by reductive amination of CH$_2$O

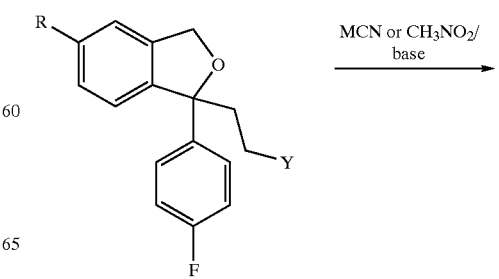

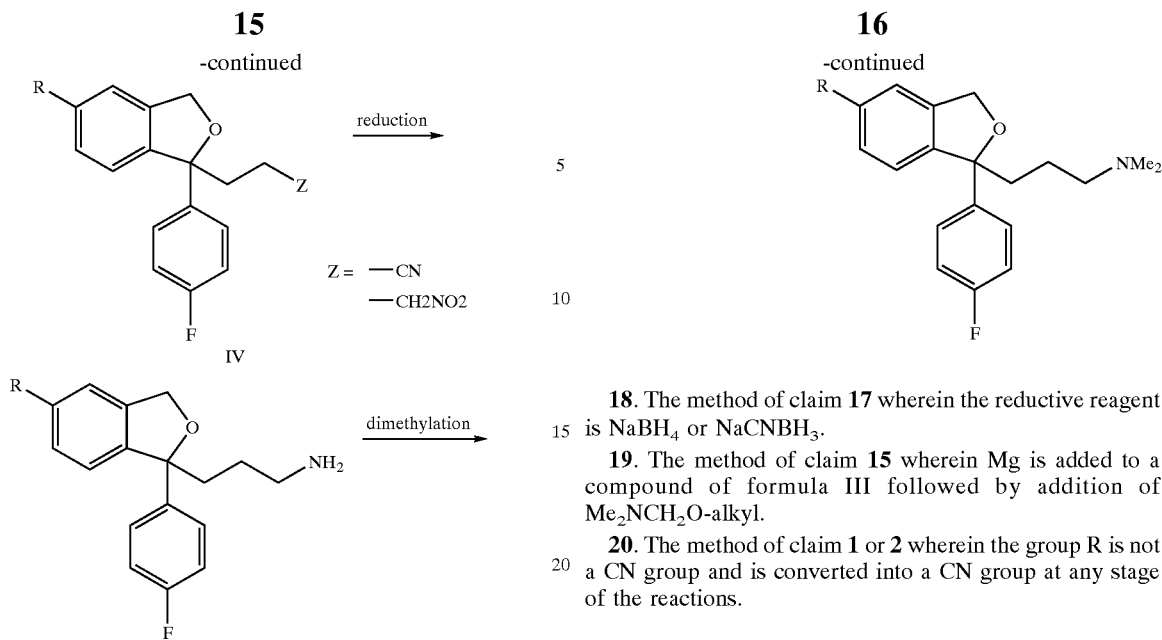
18. The method of claim 17 wherein the reductive reagent is NaBH$_4$ or NaCNBH$_3$.
19. The method of claim 15 wherein Mg is added to a compound of formula III followed by addition of Me$_2$NCH$_2$O-alkyl.
20. The method of claim 1 or 2 wherein the group R is not a CN group and is converted into a CN group at any stage of the reactions.
* * * * *